US012721828B2

(12) United States Patent
Meijlink

(10) Patent No.: US 12,721,828 B2
(45) Date of Patent: Sep. 1, 2026

(54) PHARMACEUTICAL LIQUID COMPOSITION, KIT OF PARTS COMPRISING THE PHARMACEUTICAL LIQUID COMPOSITION, AND METHOD FOR PREPARING THE PHARMACEUTICAL LIQUID COMPOSITION

(71) Applicant: MPERIUM B.V., Ankeveen (NL)

(72) Inventor: Peter Meijlink, Ankeveen (NL)

(73) Assignee: MPERIUM B.V., Ankeveen (NL)

( * ) Notice: Subject to any disclaimer, the term of this patent is extended or adjusted under 35 U.S.C. 154(b) by 1129 days.

(21) Appl. No.: 17/774,091

(22) PCT Filed: Nov. 5, 2020

(86) PCT No.: PCT/NL2020/050693
§ 371 (c)(1),
(2) Date: May 3, 2022

(87) PCT Pub. No.: WO2021/091381
PCT Pub. Date: May 14, 2021

(65) Prior Publication Data

US 2022/0387363 A1 Dec. 8, 2022

(30) Foreign Application Priority Data

Nov. 5, 2019 (NL) ..................................... 2024161

(51) Int. Cl.

| | |
|---|---|
| ***A61K 31/192*** | (2006.01) |
| ***A61K 9/08*** | (2006.01) |
| ***A61K 31/047*** | (2006.01) |
| ***A61K 31/70*** | (2006.01) |
| ***A61K 31/717*** | (2006.01) |
| ***A61K 47/10*** | (2017.01) |
| ***A61K 47/26*** | (2006.01) |
| ***A61K 47/38*** | (2006.01) |

(52) U.S. Cl.
CPC .............. *A61K 31/192* (2013.01); *A61K 9/08* (2013.01); *A61K 31/047* (2013.01); *A61K 31/70* (2013.01); *A61K 31/717* (2013.01); *A61K 47/10* (2013.01)

(58) Field of Classification Search
CPC ........ A61K 31/192; A61K 9/08; A61K 47/10; A61K 47/38; A61K 47/26
See application file for complete search history.

(56) References Cited

U.S. PATENT DOCUMENTS

| | | | |
|---|---|---|---|
| 6,806,256 B2 | 10/2004 | Ulrich et al. | |
| 8,703,156 B2 * | 4/2014 | Spino | A61K 47/10 514/312 |
| 2006/0045912 A1 | 3/2006 | Truog | |
| 2007/0004805 A1 | 1/2007 | Jobdevairakkam et al. | |
| 2011/0039897 A1 | 2/2011 | Spino et al. | |
| 2012/0115958 A1 | 5/2012 | Mariotti et al. | |

FOREIGN PATENT DOCUMENTS

| | | |
|---|---|---|
| CN | 1343489 A | 4/2002 |
| WO | 03034991 A2 | 5/2003 |
| WO | 2008083226 A2 | 7/2008 |
| WO | 2011011781 A1 | 1/2011 |
| WO | 2011143152 A2 | 11/2011 |

OTHER PUBLICATIONS

International Search Report and Written Opinion for PCT/NL2020/050693, mailed Feb. 22, 2021 (20 pages).

* cited by examiner

*Primary Examiner* — Irina Neagu
(74) *Attorney, Agent, or Firm* — KDW Firm PLLC

(57) ABSTRACT

A pharmaceutical liquid composition includes a solution of a physiologically acceptable salt of 4-phenylbutyric acid, which in one embodiment is the sodium salt of 4-phenylbutyric acid, in an aqueous medium at a concentration of at least 1.34 mmol/ml. The aqueous medium includes glycerol; a viscosity enhancing agent, where the viscosity enhancing agent includes a cellulose derivate, and water. The pharmaceutical liquid composition further includes a sweetening agent.

23 Claims, 2 Drawing Sheets

PHARMACEUTICAL LIQUID COMPOSITION, KIT OF PARTS COMPRISING THE PHARMACEUTICAL LIQUID COMPOSITION, AND METHOD FOR PREPARING THE PHARMACEUTICAL LIQUID COMPOSITION

This application is a national stage filing under 35 U.S.C. 371 of pending International Application No. PCT/NL2020/050693, filed Nov. 5, 2020, which claims priority to Netherlands Patent Application No. 2024161, filed Nov. 5, 2019, the entirety of which applications are incorporated by reference herein.

FIELD OF INVENTION

The field of the invention relates to a pharmaceutical liquid composition. The field of the invention further relates to a kit of parts comprising the pharmaceutical liquid composition. The field of the invention further relates to a method for preparing a pharmaceutical liquid composition. The field of the invention further relates to a pharmaceutical liquid composition for use as a medicament.

BACKGROUND

Generally is known a use of a sodium 4-phenylbutyrate solution in an aqueous medium as an alternative for present therapeutic treatments of certain disorders, specifically spinal muscular atrophy (SMA), central nervous system (CNS) cancer, myelodysplastic syndrome (MS), acute leukemia, glioblastoma multiforme, amyotrophic lateral sclerosis (ALS), and colon cancer.

The sodium 4-phenylbutyrate solution in an aqueous medium can be formed by dissolving a powder of sodium 4-phenylbutyrate in water. The sodium 4-phenylbutyrate can be provided as a powder for making a solution for oral administration to infants and young children, and as tablets for adults and children weighing over 20 kg. However, tablets are not easily swallowed by patients.

The powder dosage is measured in one of three differently sized measuring spoons, which may lead to an imprecise dosage level. The imprecise dosing measurement, and the need to mix the powder with a fluid for administration, leads to a lack of compliance in taking the prescribed dose at the required intervals. Consequently, it is invariably the case that children have to be admitted to hospital, sometimes two or three times a year, because they feel nauseous, and are diagnosed with signs of hyperammonemia caused by failure to maintain the dosing regimen. The symptom of nausea means the child patient cannot take the powder orally. Accordingly, in hospital the patient is treated with nasogastric or gastronomy tube administering of sodium 4-phenylbutyrate. When the nausea subsides, normal oral therapy is then resumed.

Sodium 4-phenylbutyrate is also useful for treating a variety of other medical diagnosed indications, such as benign prostate hyperplasy, certain cancers, cystic fibrosis; HIV, spinocerebellar ataxia, kidney and liver failures, and thalasemia.

Another use for sodium phenylbutyrate is to induce fetal hemoglobin production in patients with sickle cell anemia; this has been described by George J. Dover (Blood, vol. 84, No. 1, Jul. 1, 1994: pp 339-343). This paper states that sodium phenylbutyrate in powdered form has a bitter taste that, despite many attempts, cannot be taste masked. Two of the four subjects treated as outpatients reported an inability to maintain compliance with their dosing regimen because of the high dosage requirements (30 to 40 tablets per day).

US Patent Application Publication No. 2003/0195255 describes a method of administering sodium 4-phenylbutyrate orally to treat loss of mental function associated with chronic hepatic encephalopathies, recommending a high dosage of about 200-300 mg//kg initially over one to two hours, and then divided into three equal dosages daily; for adults the dose is described as 3 to 12 g/m$^2$. With regard to the synthetic of sodium 4-phenylbutyrate and related compounds, some of the methods involve using substituted malonic esters. Sodium 4-phenylbutyrate is a very bitter-tasting compound and so it is very difficult for patients to comply with their dosing regimen, especially children who have to take large amounts of the medicine every day. Administering such high dose of drug in powder form or in the form of tablet is extremely stressful to the children as it is difficult to prepare the compound in a way that is palatable to children. Patients, particularly children, tend not to comply with the dosing regimens that require multiple doses given at short intervals throughout the day as it is not easily swallowed. Although the treatment works, non compliance with the present dosing regimen causes incomplete treatment leading to occasional hospitalization.

There is thus a need for a treatment of certain disorders, specifically spinal muscular atrophy (SMA), central nervous system (CNS) cancer, myelodysplastic syndrome (MS), acute leukemia, glioblastoma multiforme, amyotrophic lateral sclerosis (ALS), and colon cancer that allows fewer doses to be given in a more readily compounded formulation to increase compliance in patients, particularly in children.

Many medical applications of a solid pharmaceutical composition containing sodium 4-phenylbutyrate are based on mixing the pharmaceutical composition with water just before administration. A disadvantage of said way of preparing a sodium 4-phenylbutyrate solution in water based on the solid pharmaceutical composition is that administering the desired dose of sodium 4-phenylbutyrate to the patient, especially a young child, may be not precise. Another disadvantage is that only sodium phenylbutyrate will dissolve, while the excipients will not. This makes it more difficult to swallow the partial solution by patients.

Another known disadvantage of an aqueous solution of sodium 4-phenylbutyrate in water is that it may suffer from limited storage stability, for instance due to being not microbiologically stable.

Thus, a need exists to provide a pharmaceutical composition containing sodium 4-phenylbutyrate as active ingredient, which pharmaceutical composition may be used daily and stored by a patient in a simple way.

SUMMARY

Embodiments of the invention aim to provide a pharmaceutical liquid composition comprising a solution of a physiologically acceptable salt of 4-phenylbutyric acid, wherein the pharmaceutical liquid composition may be used daily and stored by a patient in a simple way.

Particular embodiments aim to provide a pharmaceutical liquid composition comprising a solution of a physiologically acceptable salt of 4-phenylbutyric acid, wherein the pharmaceutical liquid composition provides a precise control on dosing of the salt of 4-phenylbutyric acid for oral administration.

Particular embodiments aim to provide a pharmaceutical liquid composition comprising a solution of a physiologically acceptable salt of 4-phenylbutyric acid, wherein the pharmaceutical liquid composition helps a patient to maintain compliance with their dosing regimen.

Particular embodiments aim to provide a pharmaceutical liquid composition comprising a solution of a physiologically acceptable salt of 4-phenylbutyric acid, wherein the pharmaceutical liquid composition is usable to administer in a way that supports a swallowing by children and/or by patients having swallowing problems.

According to a first aspect of the invention there is provided a pharmaceutical liquid composition comprising a solution of a physiologically acceptable salt of 4-phenylbutyric acid, preferably the sodium salt of 4-phenylbutyric acid, in an aqueous medium at a concentration of at least 1.34 mmol/ml (250 mg/ml SPB);

Wherein the aqueous medium comprises:

a. glycerol;

b. a viscosity enhancing agent; and c. water;

and wherein the pharmaceutical liquid composition further comprises a sweetening agent.

In a particular embodiment, the viscosity enhancing agent comprises a cellulose derivate. The cellulose derivate is a thickening aid in the aqueous medium. The cellulose derivate is dissolved in said water and glycerol of the aqueous medium and provides a thickening to the aqueous medium.

The pharmaceutical liquid composition has a concentration level of the physiologically acceptable salt of 4-phenylbutyric acid of at least 1.34 mmol/ml (250 mg/ml SPB). The concentration level of the physiologically acceptable salt of 4-phenylbutyric acid supports the use of a lower amount of solution while providing a higher amount of the salt of 4-phenylbutyric acid.

Additionally, the concentration level of the physiologically acceptable salt of 4-phenylbutyric acid of at least 1.34 mmol/ml surprisingly provides an improved microbiological stability of the pharmaceutical liquid composition. In particular, a concentration level of more than 1.61 mmol/ml (300 mg/ml SPB) further improves the microbiological stability of the pharmaceutical liquid composition. As such, no additional preservative is needed to provide a microbiological stable solution.

A concentration of the physiologically acceptable salt of 4-phenylbutyric acid in the aqueous medium (expressed in mmol/ml) according to the invention is determined by measuring the concentration of 4-phenylbutyric acid in mmol/ml using High-performance liquid chromatography (HPLC) technique. HPLC techniques to determine the concentration of 4-phenylbutyric acid in an aqueous medium are generally known. The HPLC technique may be optimized to separate the 4-phenylbutyric acid from the other components of the pharmaceutical liquid composition depending on the composition of the pharmaceutical liquid composition.

For the calculation of the concentration of the physiologically acceptable salt of 4-phenylbutyric acid in the aqueous medium (expressed in mmol/ml) it may be determined that the 4-phenylbutyric acid is substantially completely dissolved in the aqueous medium based on the salt form. Thus, the concentration of the physiologically acceptable salt of 4-phenylbutyric acid in the aqueous medium may be assumed to be substantially equal to the concentration of 4-phenylbutyric acid in the aqueous medium (in mmol/ml).

A concentration of a sodium salt of 4-phenylbutyric acid according to the invention, when being used to form the pharmaceutical liquid composition, may be calculated as a concentration expressed in mg/ml based on the determined amount of the physiologically acceptable salt of 4-phenylbutyric acid expressed in mmol/ml and based on the molar mass of sodium phenylbutyrate (i.e. 186.2 g/mol).

The combination of the glycerol and the viscosity enhancing agent provide an improved precise control on dosing of the salt of 4-phenylbutyric acid for oral administration due to an adequate control on the viscosity of the pharmaceutical liquid composition. The viscosity enhancing agent controls the viscosity of the pharmaceutical liquid composition at a level which is suitable for precise dosing of the pharmaceutical liquid composition, especially for a precise dosing of the pharmaceutical liquid composition in the range of 0.5 ml-20.0 ml per dose. In particular, a precise dosing of the pharmaceutical liquid composition is critical for infants, which require a target dosing of the active ingredient less than less than 5.0 grams per day, often between 1.0 and 5.0 grams per day depending on age, wherein the daily amount may be divided in 4 separate doses per day.

Additionally, the use of the glycerol as solvent together with water provides that the viscosity enhancing agent controls the viscosity of the pharmaceutical liquid composition, while the solution stability of the salt of 4-phenylbutyric acid in the pharmaceutical liquid composition is not adversely affected. As a result, the concentration of the salt of 4-phenylbutyric acid in pharmaceutical liquid composition remains stable over a longer time.

The use of glycerol further has been found to supports the microbiological stability of the pharmaceutical liquid composition.

Additionally, the sweetening agent supports a more palatable pharmaceutical liquid composition. It has surprisingly been found that the sweetening agent may be dissolved in the aqueous medium, without adversely affecting the solution stability of the salt of 4-phenylbutyric acid in the pharmaceutical liquid composition.

In an embodiment, the glycerol has a volume concentration of at least 1.0% w/v to the total volume of the aqueous medium, preferably in the range 1.0% w/v to 20.0% w/v relative to the total volume of the aqueous medium. 1.0% w/v corresponds to 10 g of glycerol in 1 liter total volume of the aqueous medium. 20.0% w/v corresponds to 200 g of glycerol in 1 liter total volume of the aqueous medium, The aqueous medium containing glycerol preferably has a glycerol concentration of at least 1.0% w/v to provide a suitable co-solvent for the viscosity enhancing agent. The amount of glycerol concentration is preferably less than to 20.0% w/v as a higher concentration of glycerol may have an adverse affect on stomach or intestines of the patient, such as diarrhea and flatulence.

At concentrations of 5 to 10% w/v, it is found that glycerol in a water-based solution possesses unexpected bacteriostatic and fungicidal properties.

In an embodiment, the viscosity enhancing agent comprises at least one of a cellulose derivate, xanthan gum, carageenan, polyethylenglycol and mixtures thereof.

In an embodiment, the viscosity enhancing agent comprises a cellulose derivate, the cellulose derivate being selected from the group consisting of methyl-ethyl-propyl cellulose, hydroxypropylcellulose, hydroxy ethyl cellulose, sodium carboxymethyl cellulose, microcrystalline cellulose.

In a particular embodiment, the viscosity enhancing agent comprises hydroxyethylcellulose. It has been found the a hydroxyethylcellulose may suitably control the viscosity of the pharmaceutical liquid composition at a low concentration of the viscosity enhancing agent, while not adversely affecting the solution stability of the physiologically acceptable salt of 4-phenylbutyric acid.

It has been found that a cellulose derivate, preferably a hydroxyethylcellulose, provides good solubility in water, preferably when first being dispersed or dissolved in glycerol before being added to water, and enables a control on the desired viscosity of the pharmaceutical liquid composition. A desired viscosity is in the range of 100 mPa·s-500 mPa·s at 25° C. Additionally, the cellulose derivate, when being dissolved and providing a higher viscosity, does not disturb or reduce the solution stability of the physiologically acceptable salt of 4-phenylbutyric acid. Thus, the physiologically acceptable salt of 4-phenylbutyric acid remains soluble in the pharmaceutical liquid composition, even when the physiologically acceptable salt of 4-phenylbutyric acid is present at a relatively high concentration of at least 1.34 mmol/ml.

In an embodiment, the weight ratio between glycerol and the viscosity enhancing agent is between 200:1 and 10:1. The weight ratio is relevant for providing a suitable solvent for the viscosity enhancing agent both during preparation of the pharmaceutical liquid composition and the storage of the pharmaceutical liquid composition to obtain the desired viscosity in the aqueous medium.

In an embodiment, the physiologically acceptable salt of 4-phenylbutyric acid is the sodium salt of 4-phenylbutyric acid. The physiologically acceptable salt of 4-phenylbutyric acid may be any suitable salt of 4-phenylbutyric acid for a pharmaceutical liquid composition. Particular preferred is the sodium salt of 4-phenylbutyric acid, also due to its good solubility in the aqueous medium.

Bacteria Yeasts and fungi thrive within the pH range of 5.5 to 8.0 in aqueous media. Known is that a very high or very low pH can make a product more hostile for some microbes. If the pH is high enough, for example, over pH 10, a preservative may not be needed.

In an embodiment, the physiologically acceptable salt of 4-phenylbutyric acid has a concentration in the range of 1.34 mmol/ml (250 mg/ml SPB) to 4.03 mmol/ml (750 mg/ml SPB), preferably in the range of 1.61 mmol/ml (300 mg/ml SPB) to 2.69 mmol/ml (500 mg/ml SPB), more preferably in the range of 1.61 mmol/ml (300 mg/ml SPB) to 2.15 mmol/ml (400 mg/ml SPB). The lower limit is determined by the effect of the concentration of the physiologically acceptable salt of 4-phenylbutyric acid on the microbiological stability of the pharmaceutical liquid composition.

The higher limit is mainly determined by the solution stability of the pharmaceutical liquid composition. In case a higher concentration is selected, the amount of sweetening agent present in the pharmaceutical liquid composition may be restricted and/or the solution stability of the physiologically acceptable salt of 4-phenylbutyric acid may become less.

In an embodiment, the pH of the liquid composition is in the range of 6.0 to 10.0, preferably in the range of 7.0 to 9.0, more preferably in the range of 8.0 to 9.0. The pH higher than 6.0, preferably higher than 7.0 has been found to enhance the microbiological stability of the pharmaceutical liquid composition.

It has been found that a concentration of the physiologically acceptable salt of 4-phenylbutyric acid of higher than 1.34 mmol/ml (250 mg/ml SPB), preferably higher than 1.61 mmol/ml (300 mg/ml SPB), more preferably in the range of 1.61 mmol/ml (300 mg/ml SPB) to 2.15 mmol/ml (400 mg/ml SPB), raises the pH of the pharmaceutical liquid composition higher than 6.0, preferably higher than 7.0, more preferably in the range of 8.0 to 9.0.

A sodium salt of 4-phenylbutyric acid at 1.88 mmol/ml (350 mg/mL SPB) in an aqueous solution was confirmed to be in alkaline regions, >8. The alkaline solution pH limited selection of effective and regulatory acceptable preservatives systems. Application of parabens may be rejected due to intended pediatric use and from a regulatory perspective (parabens are suspected allergen).

Unexpectedly a solution of sodium salt of 4-phenylbutyric acid of 1.88 mmol/ml (350 mg/mL SPB) has been found to be self-preserving without using additional preservative agents. The advantage is that no additional preservative agents need to be added to the pharmaceutical liquid composition.

In an embodiment, the viscosity enhancing agent has a concentration of at least 0.001 g/ml relative to the total volume of the aqueous medium, preferably in the range 0.001 g/ml to 1.000 g/ml relative to the total volume of the aqueous medium, more preferably in the range 0.001 g/ml to 0.100 g/ml relative to the total volume of the aqueous medium. The relatively low amount of viscosity enhancing agent has been found suitable for raising the viscosity, while not adversely affecting the solution stability of the physiologically acceptable salt of 4-phenylbutyric acid.

In an embodiment, the viscosity of the liquid composition is in the range of 100 mPa·s-1000 mPa·s at 25° C., preferably in the range of 100 mPa·s-500 mPa·s at 25° C. It has been found that the viscosity of the liquid composition, which is higher than of water or glycerol at 25° C., enhances a precise dosing of the pharmaceutical liquid composition. The pharmaceutical liquid composition may be administered using common syringes suitable for a dose in the range of 1.0 ml-20 ml. The accuracy of dosing is more critical for a dose in the range of 1.0 ml-5.0 ml. The accuracy of dosing the pharmaceutical liquid composition is in the range of +/−5% (at a low volume around 0.5-2.5 ml) or even better (at volumes larger than 2.5 ml). It has been found that a viscosity in the range of 100 mPa·s-1000 mPa·s at 25° C. makes the pharmaceutical liquid composition suitable to be administered to the patient using a nasogastric and/or gastronomy tube. When the viscosity is higher than 1000 mPa·s at 25° C. the use of a nasogastric and/or gastronomy tube becomes problematic.

Surprisingly, it is found that the pharmaceutical liquid composition may be reliably administered using a nasogastric and/or gastronomy tube as it is found that the solution of the physiologically acceptable salt of 4-phenylbutyric acid remains stable during the use in a nasogastric and/or gastronomy tube.

In addition, it has been found that a viscosity in the range of 100 mPa·s-500 mPa·s at 25° C. makes the pharmaceutical liquid composition suitable to be precisely dosed using a common syringes suitable for a dose in the range of 1.0 ml-20 ml. When the viscosity is higher than 500 mPa·s at 25° C. the accuracy of dosing using the syringe becomes problematic.

In an embodiment, the sweetening agent comprises a natural sweetening agent and/or an artificial sweetening agent.

Natural sweetening agents may be present in a range of 0.01% w/v to 1.00% w/v with respect to the total volume of the aqueous medium, preferably in the range of 0.01% w/v to 0.10% w/v with respect to the total volume of the aqueous medium. Artificial sweeteners may be present in a range of 0.01% w/v to 1.00% w/v with respect to the total volume of the aqueous medium, preferably in the range of 0.01% w/v to 0.10% w/v with respect to the total volume of the aqueous medium.

In an embodiment, the natural sweetener is selected from the group consisting of sucrose, dextrose, fructose, sorbitol, xylitol, vanilla, mannitol and mixtures thereof and wherein the artificial sweetener is selected from the group consisting of sodium saccharine, sodium cyclamate, aspartame, lacititol, isomalt, sucralose acesulfame K, neohespiridine, sucralose and mixtures thereof.

In an embodiment, the sweetening agent comprises aspartame having a concentration of at least 0.01 g/ml relative to the total volume of the aqueous medium, preferably in the range of 0.01-0.10 g/ml.

In an embodiment, the sweetening agent comprises sucrose having a concentration of at least 0.01 g/ml relative to the total volume of the aqueous medium, preferably in the range of 0.01-0.10 g/ml.

In an embodiment, the sweetening agent comprises aspartame and sucrose and wherein the concentration of aspartame relative to the concentration of sucrose is in the range 1:2 to 2:1.

The combination of the aspartame and sucrose in said ratio provides an enhanced sweetening effect. In particular, the sweetening is provided both for the short term taste and longer term aftertaste.

In an embodiment, the viscosity enhancing agent comprises a hydroxyethylcellulose having a weight average molecular weight in the range of 200.000-2.000.000 Da.

According to another aspect of the invention there is provided a kit of parts comprising:

a. a pharmaceutical liquid composition according to the present invention; and
b. at least one flavouring liquid concentrate, the flavouring liquid concentrate comprising at least one flavouring agent.

The kit of parts provides a combination of the pharmaceutical liquid composition of the invention and at least one flavouring liquid concentrate. The at least one flavouring liquid concentrate can be administered in drops, such as administered in drops to a mixture containing water and the pharmaceutical liquid composition to obtain a flavoured pharmaceutical liquid mixture.

A flavouring liquid concentrate according to the present invention is liquid at room temperature. As such, the flavouring liquid concentrate can easily be administered in drops.

The flavour of a poor tasting pharmaceutical ingredient agent in a liquid dosage form is inevitably detected during the drinking process or immediately after swallowing. Therefore, it is important to mask the often disagreeable taste of the active ingredient during the time that the medicine is in the mouth and/or after administration. This invention relates to a kit of new taste-masking platform compositions wherein the taste and/or aftertaste of a pharmaceutical active ingredient is reduced to an acceptable level. This invention further relates to taste-masked pharmaceutical compositions containing emphasized and offensive sour/salty/sweet/bitter tastes and/or aftertaste.

The at least one flavouring liquid concentrate may be used to improve the taste by masking a bad taste of the pharmaceutical liquid composition. As the pharmaceutical liquid composition already contains the sweetening agent, the at least one flavouring liquid concentrate may be mainly comprised of flavouring agents. The flavouring agents may be highly concentrated extracts of natural flavouring compositions or may be synthetic flavouring agent.

A flavouring agent in the context of the invention comprises a flavor essence or flavor component. Additionally, the flavouring agent may contain a carrier fluid which is configured for stabilizing the flavor essence or flavor component. The carrier fluid may in examples be a glycol, such as propylene glycol, an alkyl alcohol, an aryl alcohol and mixtures thereof. Generally, the carrier fluid may be selected to maintain a stability of the flavor essence or flavor component for at least 6 months at room temperature.

The combination of the sweetening agent contained in the pharmaceutical liquid composition and the flavouring agents of the flavouring liquid concentrate provide the taste masking effect.

The at least one flavouring liquid concentrate may easily mix and dissolve in the pharmaceutical liquid composition or in a mixture containing water and the pharmaceutical liquid composition.

As the sweetening agents are already dissolved in the pharmaceutical liquid composition, a mixture of water, the pharmaceutical liquid composition and at least one flavouring liquid concentrate is ready to be used directly after adding drops of flavouring liquid concentrate.

A mixture containing water and the pharmaceutical liquid composition may be prepared by mixing an amount of water and an amount of pharmaceutical liquid composition. The mixing ratio between pharmaceutical liquid composition and water may be in the range of 1:1-1:20, preferably in the range of 1:2-1:10. For example, a 1.0 ml pharmaceutical liquid composition may be mixed with 5.0 ml water (1:5) or may be mixed with 10.0 ml water (1:10).

The amount of the at least one flavouring liquid concentrate can be suitably selected to adjust the flavor of the pharmaceutical liquid mixture to obtain a personalized medication for the user.

The flavoured pharmaceutical liquid mixture provides improved personal palatable use to children and patients and may support children and patients to maintain compliance with their dosing regimen.

In an embodiment, the flavouring liquid concentrate is substantially free of a sweetening agent.

As the pharmaceutical liquid composition may comprises an effective amount of sweetening agents for sweetening the pharmaceutical liquid composition, the flavouring liquid concentrate may be substantially free of a sweetening agent. In particular, the at least one flavouring liquid concentrate may consist essentially of flavouring agents.

Sweetening agents are primarily solid at room temperature and need a sufficient amount of solvent to provide a liquid solution state. Adding a sweetening agent to the flavouring liquid concentrate would require a bigger amount of solvent to provide and maintain a liquid solution state.

In an embodiment, each flavouring agent has a concentration in the range of 5-100 weight-% of the total weight of the flavouring liquid concentrate. In a particular embodiment, the sum of the at least one flavouring agent is in the range of 80-100 weight-%, of the total weight of the flavouring liquid concentrate.

In an embodiment, a flavouring liquid concentrate comprises a first flavouring agent and a second flavouring agent. A combination of the first flavouring agent and the second flavouring agent may provide a better taste, for instance by combining several beneficial tastes.

In an embodiment, the kit comprises a medical dropper for administering drops of the at least one flavouring liquid concentrate. The medical dropper may be used to administer drops of the at least one flavouring liquid concentrate. Preferably, each of the flavouring liquid concentrates is contained in a small container, such as a bottle, wherein the bottle further is provided with a medical dropper.

In an embodiment, each of the at least one flavouring agent is selected from the group consisting of fruit, mint, ginger, caramel, liquorice, peppermint and eucalyptol flavours and mixtures thereof.

The fruit flavour may be selected from the group consisting of blackcurrant, apple, pear, peach, berry, wildberry, date, blueberry, kiwi, strawberry, raspberry, cherry, plum, pineapple, mango, apricot and citrus oils such as lemon, orange, lime and grapefruit oils, and mixtures thereof.

In an embodiment, the flavouring liquid concentrate comprises a first flavouring agent and a second flavouring agent, wherein: the first flavouring agent is a peppermint flavour or mint flavour; and the second flavouring agent is a fruit flavour, optionally being selected from the group consisting of mango, orange, blackcurrant and lemon.

In a further aspect a method is provided for preparing a pharmaceutical liquid composition comprising an aqueous medium wherein the aqueous medium comprises glycerol and water, wherein the pharmaceutical liquid composition is according to the invention, the method comprising the steps of:

a. providing glycerol;

b. adding the viscosity enhancing agent to the glycerol, while stirring the glycerol to form a mixture of viscosity enhancing agent and glycerol;

c. providing a solution of a physiologically acceptable salt of 4-phenylbutyric acid, preferably the sodium salt of 4-phenylbutyric acid, in water;

d. adding the solution of the physiologically acceptable salt of 4-phenylbutyric acid to the mixture of viscosity enhancing agent and glycerol, while stirring said mixture to form a solution of the physiologically acceptable salt of 4-phenylbutyric acid in the aqueous medium;

and wherein the physiologically acceptable salt of 4-phenylbutyric acid has a concentration of at least 1.34 mmol/ml (250 mg/ml SPB) in the aqueous medium.

In an embodiment, the viscosity enhancing agent selected comprises a cellulose derivate, the cellulose derivate being selected from the group consisting of methyl-ethyl-propyl cellulose, hydroxypropylcellulose, hydroxy ethyl cellulose, sodium carboxymethyl cellulose, microcrystalline cellulose, wherein preferably the viscosity enhancing agent comprises hydroxyethylcellulose.

In an embodiment, the amount of viscosity enhancing agent added to the glycerol during step b. is selected such that the concentration of the viscosity enhancing agent in the resulting mixture is in the range of 0.01 g/ml to 0.10 g/ml, preferably in the range of 0.02 g/ml to 0.08 g/ml. The amount of viscosity enhancing agent is sufficient to provide the required viscosity of the pharmaceutical liquid composition after step d. adding the solution of the physiologically acceptable salt of 4-phenylbutyric acid to the mixture of viscosity enhancing agent and glycerol. The concentration of the viscosity enhancing agent in glycerol is adequate to disperse the viscosity enhancing agent in glycerol. The dispersed viscosity enhancing agent in glycerol may subsequently easily be dissolved by a swelling process in an aqueous medium containing water and glycerol, by adding the solution of the physiologically acceptable salt of 4-phenylbutyric acid in water.

In an embodiment, the stirring in step b. is carried out continuously. The stirring process enhances a fine dispersion of the viscosity enhancing agent in glycerol.

In an embodiment, the providing of the solution of step c. comprises the steps of:

i. providing water;

ii. adding the physiologically acceptable salt of 4-phenylbutyric acid to the water, while stirring the water.

In an embodiment, further comprising the step of:

e. allowing the aqueous medium to swell, while stirring the aqueous medium.

The step of allowing the aqueous medium to swell according to the present invention is defined as a dissolving process of the dispersed viscosity enhancing agent, while controlling the viscosity of the aqueous medium to be raised, such as raised to a viscosity in the range of 100 mPa·s-500 mPa·s at 20° C.

The step of allowing the aqueous medium to swell is carried out after the adding step d. The time to allow the aqueous medium to swell may be minutes, and may be depending on temperature and stirring speed. In an example, a time of step e. to allow the aqueous medium to swell may in the range 2-30 minutes, preferably 5-20 minutes.

The stirring of the aqueous medium enhances the swelling process and may shorten the time for the aqueous medium to swell.

In an embodiment, wherein the viscosity enhancing agent is dispersed in glycerol when adding the solution of the physiologically acceptable salt of 4-phenylbutyric acid to the mixture of viscosity enhancing agent and glycerol. Without restricting the invention it is believed that the dispersed viscosity enhancing agent may have absorbed an amount of glycerol. The dispersion of the viscosity enhancing agent in glycerol enhances an appropriate swelling of the viscosity enhancing agent in an aqueous medium containing water and glycerol to dissolve the viscosity enhancing agent, without disturbing a solution stability of the physiologically acceptable salt of 4-phenylbutyric acid, such as sodium phenylbutyrate, in the aqueous medium containing water and glycerol.

It has been found that a cellulose derivate, preferably a hydroxyethylcellulose, provides good solubility in water, preferably when first being dispersed or dissolved in glycerol before being added to water, and enables a control on the desired viscosity of the pharmaceutical liquid composition. During swelling process in the aqueous medium the cellulose derivate is substantially completely dissolved in the aqueous medium. A desired viscosity is in the range of 100 mPa·s-500 mPa·s at 25° C. Additionally, the cellulose derivate, when being dissolved and providing a higher viscosity, does not disturb or reduce the solution stability of the physiologically acceptable salt of 4-phenylbutyric acid. Thus, the physiologically acceptable salt of 4-phenylbutyric acid remains soluble in the pharmaceutical liquid composition, even when the physiologically acceptable salt of 4-phenylbutyric acid is present at a relatively high concentration of at least 1.34 mmol/ml.

In an embodiment, further comprising the step of:

f. adding a sweetening agent to the solution of a physiologically acceptable salt of 4-phenylbutyric acid in water before step d. forming the solution of the physiologically acceptable salt of 4-phenylbutyric acid in the aqueous medium.

The addition of the sweetening agent before step d. is advantages to dissolve the sweetening agent in the aqueous medium as the sweetening agent is more easily dissolved in water before allowing the aqueous medium to swell (wherein the viscosity of the aqueous medium is raised to a level higher than a viscosity of water).

In a further aspect a pharmaceutical liquid composition is provided for use as a medicament.

In a further aspect a pharmaceutical liquid composition is provided for use in a method for preventing and/or treating a genetic disorder of a patient.

In an embodiment, the pharmaceutical liquid composition is administered using a nasogastric and/or gastronomy tube. Surprisingly, it is found that the pharmaceutical liquid composition may be reliably administered using a nasogastric and/or gastronomy tube as it is found that the solution of the physiologically acceptable salt of 4-phenylbutyric acid remains stable during the use in a nasogastric and/or gastronomy tube.

In an embodiment, the pharmaceutical liquid solution is administered to a patient in need thereof, the administering comprising:

a. adding an amount of the pharmaceutical liquid composition to water to form a mixture, wherein the volume ratio between the pharmaceutical liquid composition and water is in the range of 1:20 to 1:1, preferably in the range of 1:10 to 1:2.
b. Orally, preferably daily, administering said mixture to the patient.

In an embodiment, the pharmaceutical liquid composition is used for daily administering to the patient, preferably in a dose of a therapeutically effective amount of the pharmaceutical liquid composition, more preferably in three or more equally divided liquid doses.

In an embodiment, the amount of the pharmaceutical liquid composition added in step a. to water is in the range 0.5 ml to 20.0 ml.

In an embodiment, the pharmaceutical liquid composition is part of a kit of parts according to the invention, the method further comprising a step before the oral administering step of;

c. adding an amount of one or more of said at least one flavouring liquid concentrate, preferably in the form of drops of the at least one flavouring liquid concentrate, to the mixture of step a. or to the water, which is used in step a. to form the mixture.

the amount of each of said at least one flavouring liquid concentrate added is in the range of 0.01 ml-1.00 ml, preferably in the range of 0.02 ml-0.50 ml [1 drop-10 drops], more preferably in the range of 0.02 ml-0.25 ml [1 drop-5 drops].

In an embodiment, the kit of parts comprises at least two flavouring liquid concentrates and wherein the step of adding one or more flavouring liquid concentrates comprises selecting an amount of drops of a first flavouring liquid concentrate and selecting an amount of drops of a second flavouring liquid concentrate.

The amount of drops may be in the range of 1 to 10 drops of flavouring liquid concentrate, preferably in the range of 1 to 5 drops of flavouring liquid concentrate. The amount of drops is an accurate way to administer the flavouring liquid concentrate.

BRIEF DESCRIPTION OF THE FIGURES

The accompanying drawings are used to illustrate presently preferred non-limiting exemplary embodiments of devices of the present invention. The above and other advantages of the features and objects of the invention will become more apparent and the invention will be better understood from the following detailed description when read in conjunction with the accompanying drawings, in which.

MEASUREMENT METHODS

Viscosity

Figure 1:
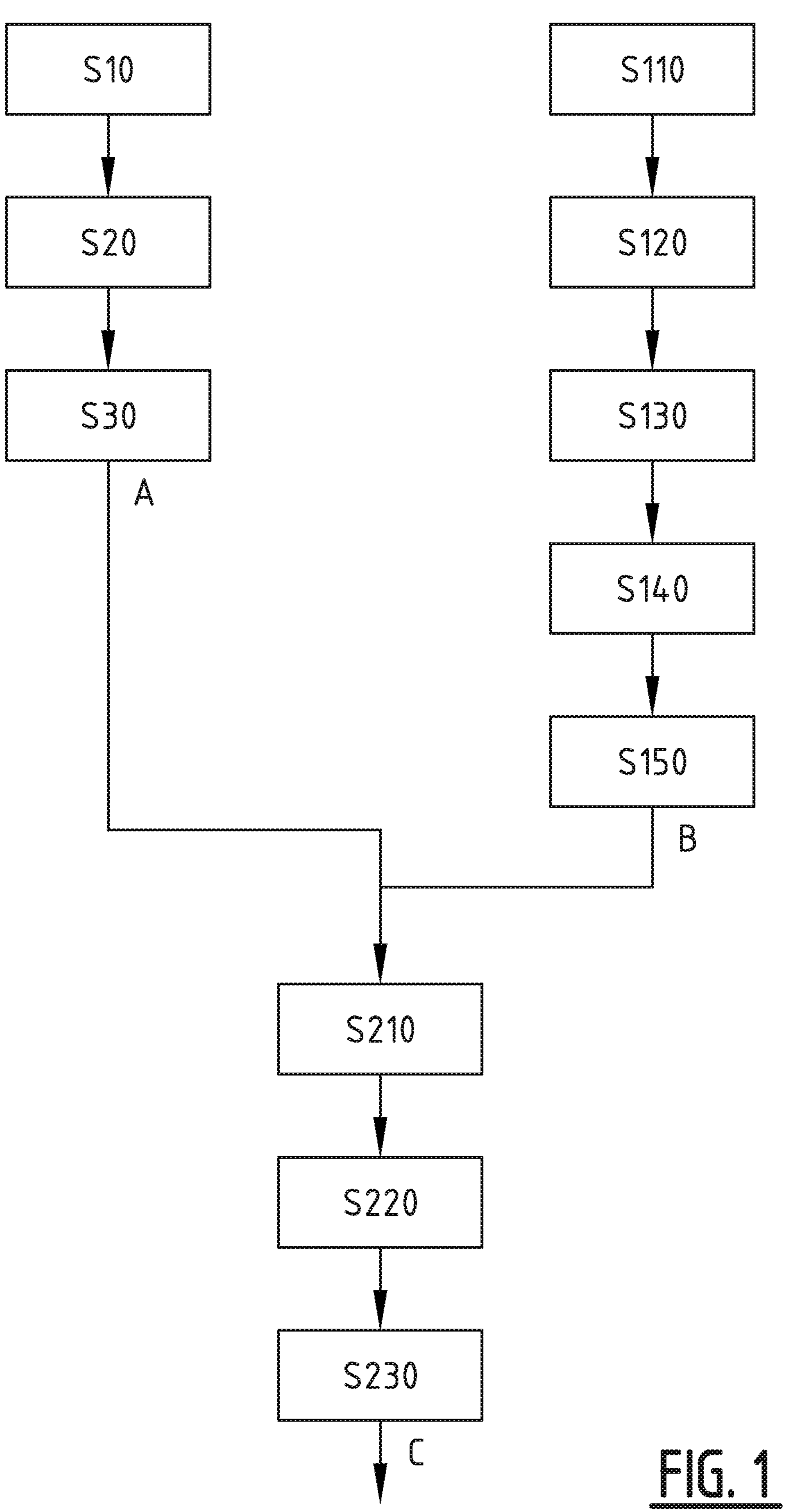
FIG. 1 illustrates schematically a process flow for preparing the pharmaceutical liquid composition of an exemplary embodiment.

Viscosity measuring low-viscous Newtonian fluids using Haake viscotester type D. Haake complies to ISO 2555. Measuring temperature is 20° C., Haake standard spindles are applied (type L1 to L4). Rotational speed: between 0.1 rpm and 200 rpm, measuring viscosity range: between 15 mPas-2.000.000 mPas.

Microbiological Stability

According to Assay and Stability methods described in US Pharmacopeia-National Formulary (USP/NF), the European Pharmacopoeia (EP).

Constitution/Concentration Stability

According to Assay and Stability methods described in US Pharmacopeia-National Formulary (USP/NF), the European Pharmacopoeia (EP).

Formulation Example

Pharmaceutical Liquid Compositions

Pharmaceutical liquid composition A is a Sodium Phenylbutyrate 350 mg/mL taste masked aqueous solution composition per liter:

| A | Ingredient | Quantity (gram) |
|---|---|---|
| 1 | Sodium Phenylbutyrate | 350 |
| 2 | Purified water | 648.15 |
| 3 | Aspartame | 2 |
| 4 | Sucralose | 2 |
| 5 | Glycerol 100% | 100 |
| 6 | Natrosol 250 HX Pharm* | 4 |
| | 1 liter= | 1106.15 |

*Hydroxyethylcellulose

The Sodium Phenylbutyrate may be abbreviated as SPB in the description. Natrosol 250 HX Pharm has a weight average Mw of 1.000.000 Da.

Natrosol 250 HX Pharm is a hydroxyethylcellulose. Said hydroxyethylcellulose may be dispersed in glycerol and may then dissolve readily in cold or hot water to form clear and smooth solutions. Furthermore, it does not precipitate even when heated.

Several alternative liquid compositions B-D were made having the same composition, however having the following concentrations of Sodium Phenylbutyrate: 200 mg/mL (B), 160 mg/mL (C) and 120 mg/mL (D).

It has been found that the cellulose derivate is suitable for thickening the pharmaceutical liquid composition and controlling the viscosity of the pharmaceutical liquid composition, while not disturbing a solubility of the physiologically acceptable salt of 4-phenylbutyric acid. In addition, the solubility and thickening effect of the cellulose derivate remains substantially unaffected by a pH of the pharmaceutical liquid composition, which may be in alkaline pH regions (i.e. >7.0) for higher concentrations of the physiologically acceptable salt of 4-phenylbutyric acid.

Furthermore, it has been found that Xanthan gum is not suitable for thickening the pharmaceutical liquid composition and controlling the viscosity of the pharmaceutical liquid composition. Xanthan gum has been found to be insufficiently soluble in water. As such, it is expected that Xanthan gum may disturb a solubility of the physiologically acceptable salt of 4-phenylbutyric acid.

Furthermore, it has been found that carbomers (carboxyvinyl polymers) are not not suitable for thickening the pharmaceutical liquid composition and controlling the viscosity of the pharmaceutical liquid composition. The carbomers are not compatible to the pharmaceutical liquid composition having a physiologically acceptable salt of 4-phenylbutyric acid of at least 1.34 mmol/ml, such as at least 250 mg/ml for sodium 4-phenylbutyric acid.

A concentration of the sodium salt of 4-phenylbutyric acid in the aqueous medium may be determined based on the dry weight of sodium 4-phenylbutyric acid in grams (or milligrams [mg]) with respect to a volume of the aqueous medium in liters (or milliliter [ml]).

A concentration of a physiologically acceptable salt of 4-phenylbutyric acid in the Pharmaceutical liquid composition may be determined or assessed by measuring the concentration of 4-phenylbutyric acid in mmol/ml using High-performance liquid chromatography (HPLC) technique. HPLC techniques to determine the concentration of 4-phenylbutyric acid in an aqueous medium are generally known. The HPLC technique may be optimized to separate the 4-phenylbutyric acid from the other components of the pharmaceutical liquid composition depending on the composition of the pharmaceutical liquid composition. Additionally, it may be checked by known techniques that substantially an equal amount of sodium (expressed in mmol/ml) as the 4-phenylbutyric acid (expressed in mmol/ml) is present in the pharmaceutical liquid composition.

Kit Compositions

The kit is comprised of a pharmaceutical liquid composition according to the invention, such as the Pharmaceutical liquid composition A described above, and one or more flavouring liquid concentrate compositions.

Figure 2:
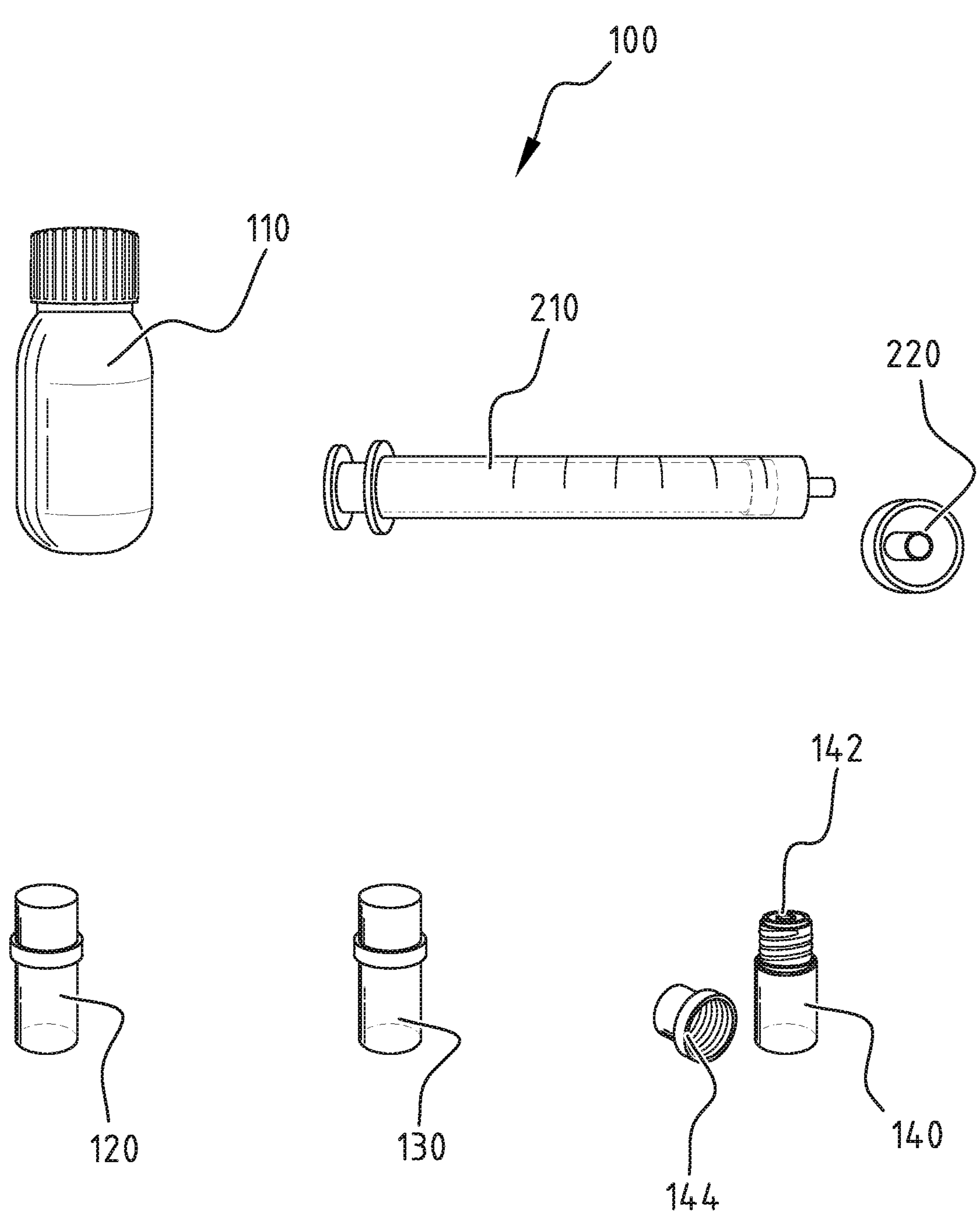
FIG. 2 illustrates schematically individual components of a flavouring pharmaceutical liquid kit.

FIG. 2 shows a kit 100 including a pharmaceutical liquid composition 110 and three flavouring liquid concentrate compositions 120, 130, 140. The pharmaceutical liquid composition 110 is contained in a bottle, such as a glass bottle. The bottle may contain a volume in the range of 50 ml, 100 ml or 200 ml of the pharmaceutical liquid composition. Optionally a medical syringe 210 may be provided to administer the pharmaceutical liquid composition 110 in an amount of 0.5 ml-20.0 ml. The medical syringe 210 can be used together with an insert 220, which can be inserted in the bottle 110, to accurately Preferably, to eliminate common errors in dosing pharmaceutical liquid compositions a specially dosing device is selected, i.e. an oral syringe fitted with a volume dosing (mL) scale and/or a corresponding active substance scale (mg).

Example: a newborn approx. 3.4 kg in body weight theoretically requires 4.8 mL undiluted of the pharmaceutical composition/day –measured with an accuracy in the range of +/−5% (at a low volume around 0.5-2.5 ml) or even better (at volumes larger than 2.5 ml). The same oral syringe is fitted with an active substance corresponding weight scale (mg). In this case measuring 4.8 mL corresponds with a 1.7 g active substance dose. Where the corresponding active substance weight (mg) correlates with the active substance concentration of the pharmaceutical liquid composition.

Each of the three flavouring liquid concentrate compositions 120, 130, 140 is contained in a smaller bottle, such as a glass bottle. The bottle may contain 3 ml-10 ml of the flavouring liquid concentrate composition. Each bottle of the flavouring liquid concentrate has a cap 144 and may further contain a medical dropper, such as a dropper insert 142, to administer drops of the flavouring liquid concentrate.

In alternative embodiments, the kit 100 may have one flavouring liquid concentrate composition contained in a bottle, may have two flavouring liquid concentrate compositions individually packed in a bottle, or any other suitable number of flavouring liquid concentrate composition individually packed in a bottle.

Flavouring Liquid Concentrate Compositions

Batch formula; —Mango-Orange drops—inactive ingredient—topping flavor composition A

| | Ingredient | Quantity (p/gram) | Quantity (g) p/100 mL batch (100 mL = ±92 g) |
|---|---|---|---|
| 1 | Mango CRA 1221L | 0.495 | 45.54 |
| 2 | Orange CRA 1028L | 0.388 | 35.81 |
| 3 | Peppermint CRA 1418L | 0.117 | 10.79 |
| | | 1.000 | 92.33 |

Batch formula; — Blackcurrant drops—inactive ingredient—topping flavor composition B

| | Ingredient | Quantity (p/gram) | Quantity (g) p/100 mL batch (100 mL = ±96 g) |
|---|---|---|---|
| 1 | Blackcurrant CRA 1198L | 0.885 | 84.96 |
| 2 | Peppermint CRA 1418L | 0.115 | 11.04 |
| | | 1.000 | 96.00 |

Batch formula; — Lemon—Mint drops—inactive ingredient—topping flavor composition C

| | Ingredient | Quantity (p/gram) | Quantity (g) p/100 mL batch (100 mL = ±87 g) |
|---|---|---|---|
| 1 | Lemon CRA 1190L | 0.794 | 69.44 |
| 2 | Peppermint CRA 1418L | 0.206 | 18.06 |
| | | 1.000 | 87.50 |

Methods for Preparing the Compositions

Pharmaceutical Liquid Composition

Equipment: stainless steel tanks (2), propeller stirrer (preferably portable), bottles filling line Description of the Manufacturing Process:

1. Dispense raw materials
2. Fill a suitable primary stainless steel tank with the Glycerol 100%
3. Gradually add and disperse the Natrosol 250 HX Pharm in the Glycerol, whilst stirring continuously
4. Verify visually if the Natrosol 250 HX Pharm is homogeneously dispersed
5. Fill a suitable secondary stainless steel tank with the available purified water
6. Gradually (step-by-step) add and dissolve the Sodium Phenylbutyrate in the Purified water, whilst stirring continuously
7. Verify visually if the Sodium Phenylbutyrate is completely dissolved 8. Gradually add and dissolve the Aspartame and Sucralose whilst stirring continuously
9. Verify visually if the Aspartame and Sucralose is completely dissolved
10. Gradually add the Sodium Phenylbutyrate/Aspartame/Sucralose solution to the primary tank with the Glycerol 100%/Natrosol 250 HX Pharm dispersion, whilst stirring continuously
11. Allow the complete solution to swell for several minutes (Example: 10-15 min at 2 liter scale), whilst stirring continuously
12. Verify visually if the final solution is homogeneous and clear
13. Sample the bulk solution for in-process analysis prior to filling, verifying assay Sodium Phenylbutyrate
14. Fill the bulk solution into selected bottles
15. Sample filled bottles for final product QC release analysis according to product specifications
16. Label the bottles A workflow for a process of preparing the pharmaceutical liquid composition according to an embodiment is shown in FIG. 1.

In step S10 a first tank is provided with glycerol. In step S20 a viscosity enhancing agent, preferably a cellulose derivate, in an example Natrosol 250 HX, is gradually added and dispersed in the glycerol, while stirring the glycerol continuously.

In step S30 it is verified, such as visually, that the viscosity enhancing agent is homogeneously dispersed in the glycerol. After step S30 a mixture A of viscosity enhancing agent and glycerol is provided, wherein the viscosity enhancing agent is dispersed in glycerol.

In step S110 a second tank is provided with purified water. In step S120 a physiologically acceptable salt of 4-phenylbutyric acid, such as sodium phenylbutyrate, is gradually added and dissolved in the water, while stirring the solution continuously.

In step S130 it is verified, such as visually, that the salt of 4-phenylbutyric acid is dissolved in water.

In step S140 at least one sweetening agent, such as aspartame and/or sucrose, is gradually added and dissolved, while stirring the solution continuously. In step S150 it is verified, such as visually, that the sweetening agent or sweetening agents is/are dissolved in water. After step S150 a solution B of salt of 4-phenylbutyric acid and sweetening agent in water is provided.

In step S210 the solution B is gradually added to the mixture A of viscosity enhancing agent and glycerol, while stirring the mixture continuously. After adding the solution B, in step S220 the aqueous medium of the mixture is allowed to swell for minutes, while stirring the aqueous medium continuously. In step S230 it is verified, such as visually, that the final solution C is homogeneous and clear. The viscosity enhancing agent is completely dissolved in the aqueous medium.

In an example, the solution B has a concentration of sodium phenylbutyrate such that the concentration of sodium phenylbutyrate in the solution C is at least 250 mg/ml.

Flavouring Liquid Concentrate Compositions

Manufacturing Method;

Equipment: Erlenmeyer flask with cover, portable lab-scale propeller stirrer, bottles filling equipment. Note: possibility to flush Erlenmeyer flask and bottles with Nitrogen (prior/during mixing/filling)

Description of the Manufacturing Process:

1. Dispense raw materials
2. Flush the Erlenmeyer flask with nitrogen prior to adding ingredients and close the flask
3. Open the flask briefly and add the liquid flavoring agents, flush the tank again with nitrogen
4. Close the flask directly after and mix ingredients for approx. 10 minutes
5. Verify visually if the blend is homogeneous, sample the mixture for release
6. Flush the flask again with nitrogen and close the flask
7. Fill the bulk mixture into selected bottles, whilst flushing with nitrogen
8. Sample filled bottles for final product QC release analysis according to product specifications
9. Label the bottle Properties Solution Stability Testing of solubility of Sodium Phenylbutyrate (SPB) in purified water at concentrations of 500 mg/ml, 450 mg/ml, 400 mg/ml and 350 mg/ml demonstrated that the latter concentration was the most efficient concentration for implementation in a conventional manufacturing process. SPB concentrations higher than 350 mg/ml created significant lumping of the SPB during the dissolving process.

For the 500 mg/ml concentration it was even required to pre-heat (40° C.) the purified water to dissolve the SPB completely.

Test Procedure 500 mg/ml (required pre-heating of water), 450 mg/ml, 400 mg/ml and 350 mg/ml solutions were packed in clear glass bottles and stored for 2 weeks at 25° C., 40° C. and 5° C. Only the SPB 500 mg/ml showed crystallization after 1 week at 40° C.

Considering the technical difficulties associated with dissolving SPB at concentrations higher than 350 mg/ml, it was concluded that the risk of creating a near saturated SPB solution above the 350 mg/ml concentration was present.

This selection is particularly relevant because the previous represents a baseline formulation to which a number of additional (taste masking) supportive inactive ingredients required to completely dissolve in the available aqueous component of the formulation.

Comparison Experiments

Two potentially suitable preservative systems, known to be effective in alkaline pH regions, were identified and analyzed for compatibility in prototype sodium salt of 4-phenylbutyric acid 350 mg/mL aqueous solution formulation A, i.e. chlorhexidine diacetate (0.5% g/v) and Domiphen bromide (0.5% g/v).

The prototype solutions contained 4-phenylbutyric acid 350 mg/mL in combination with the chlorhexidine diacetate (0.5% g/v) or Domiphen bromide (0.5% g/v), respectively, dissolved in water.

Prototype solution samples stored at room temperature were analyzed for sodium salt of 4-phenylbutyric acid assay at time points T=0, T=24 hours and T=48 hours and results showed a decrease in assay over 48 hours, these preservatives were rejected because of suspected interactions between the active compound and selected preservatives and for regulatory reasons.

Preservative Effect of Pharmaceutical Liquid Composition

Conducted Preservative Efficacy Tests (PET) and Bioburden tests with formulations, containing SPB 350 mg/mL (formulation A), 200 mg/mL (formulation B), 160 mg/mL (formulation C) and 120 mg/mL (formulation D) unexpectedly confirmed self-preserving properties of SPB in aqueous solutions for an the formulations A-D. Unexpected results because in theory the alkaline pH of the solution by itself would not be sufficient.

Challenge tests have been carried out with all formulations A-D (which additionally contained lemon mint and mango orange flavour components). All formulations A-D passed the Challenge tests.

Supportive bacteriostatic, fungicidal properties of glycerol were considered to substantiate self-preserving properties of SPB 350 mg/mL, 200 mg/mL, 160 mg/mL and 120 mg/mL in aqueous solutions.

Tube Feeding Stability

A 6 hour test has been performed wherein a SPB oplossing (350 mg/ml) was circulated at room temperature by a Watson-Marlow 505-S pump, tube diameter 0.2 mm, rpm 50. The pump settings correspond to an almost dropwise output. The speed was controlled to be low to simulate a worst case situation to signal blocking of the tube and/or crystallization of the SPB solution in the tube.

Blockage of the tube and crystallization of the SPB solution in the tube did not occur during the 6 hours test procedure.

An enteral tube may be composed of PUR or silicone, but may also be composed of latex or PVC.

Viscosity

The measurement gave the following results:

Dynamic viscosity of water is 1.00 mPa-s at 20° C.

Dynamic viscosity of glycerol is 1.31 mPa-s at 20° C.

Dynamic viscosity of glycerol-water mixture (at 10% w/v) is 1.36 mPa-s at 20° C.

Dynamic viscosity of Pharmaceutical liquid compositions A is about 250 mPa-s at 20° C.

Flavouring Liquid Concentrate Drops

The Flavouring liquid concentrates may be dosed in drops by a medical dropper in drop volumes corresponding to 20-40 drops per mL. The drops have a weight in the range of 15 mg to 50 mg per drop.

It should be appreciated by those skilled in the art that any block diagrams herein represent conceptual views of illustrative units or modules embodying the principles of the invention.

Whilst the principles of the invention have been set out above in connection with specific embodiments, it is to be understood that this description is merely made by way of example and not as a limitation of the scope of protection which is determined by the appended claims.

The invention claimed is:

1. A pharmaceutical liquid composition comprising a solution of a physiologically acceptable salt of 4-phenylbutyric acid, in an aqueous medium at a concentration of at least 1.34 mmol/ml and pH>8;

wherein the aqueous medium comprises:

a. glycerol, having a volume concentration of at least 1.0 ml/l relative to the total volume of the aqueous medium;

b. a viscosity enhancing agent, wherein the viscosity enhancing agent comprises hydroxyethylcellulose as the only cellulose derivate; and c. water; and wherein the pharmaceutical liquid composition further comprises a sweetening agent, wherein the sweetening agent comprises a natural sweetening agent and/or an artificial sweetening agent, wherein the natural sweetener is selected from the group consisting of sucrose, dextrose, fructose, sorbitol, xylitol, vanilla, mannitol and mixtures thereof and wherein the artificial sweetener is selected from the group consisting of sodium saccharine, sodium cyclamate, aspartame, lacititol, isomalt, sucralose acesulfame K, neohespiridine, sucralose and mixtures thereof, and wherein the weight ratio between the glycerol and the viscosity enhancing agent is between 200:1 and 10:1.

2. The pharmaceutical liquid composition according to claim 1, wherein the pH of the liquid composition is less than or equal to 10.0.

3. The pharmaceutical liquid composition according to claim 1, wherein the viscosity enhancing agent has a concentration of at least 0.001 g/ml relative to the total volume of the aqueous medium.

4. The pharmaceutical liquid composition according claim 1, wherein the viscosity of the liquid composition is in the range of 100 mPa·s-1000 mPa·s at 25° C.

5. The pharmaceutical liquid composition according to claim 1, wherein the sweetening agent comprises aspartame.

6. The pharmaceutical liquid composition according claim 1, wherein the hydroxyethylcellulose has a weight average molecular weight in the range of 200.000-2.000.000 Da.

7. A kit of parts comprising:

a pharmaceutical liquid composition according to claim 1; and at least one flavouring liquid concentrate, the flavouring concentrate comprising at least one flavouring agent.

8. The kit of parts according to claim 7, wherein each flavouring agent has a concentration in the range of 5-100 weight-% of the total weight of the flavouring liquid concentrate and the sum of the at least one flavouring agent is in the range of 80-100 weight-% of the total weight of the flavouring liquid concentrate.

9. The kit of parts according to claim 7, wherein the kit comprises a medical dropper for administering drops of the at least one flavouring liquid concentrate.

10. The kit of parts according to claim 7, wherein each of the at least one flavouring agent is selected from the group consisting of a fruit flavour, mint, ginger, caramel, liquorice, peppermint and eucalyptol flavours and mixtures thereof.

11. A method for preparing the pharmaceutical liquid composition of claim 1, the method comprising the steps of:

a. providing glycerol;

b. adding the viscosity enhancing agent comprising hydroxyethylcellulose to the glycerol, while stirring, to form a mixture of viscosity enhancing agent comprising hydroxyethylcellulose and glycerol;

c. providing a solution of a physiologically acceptable salt of 4-phenylbutyric acid in water;

d. adding the solution of the physiologically acceptable salt of 4-phenylbutyric acid to the mixture of viscosity enhancing agent comprising hydroxyethylcellulose and glycerol, while stirring, to form a solution of the physiologically acceptable salt of 4-phenylbutyric acid in the aqueous medium;

e. optionally allowing the aqueous medium to swell, while stirring the aqueous medium; and f. optionally adding a sweetening agent to the solution of a physiologically acceptable salt of 4-phenylbutyric acid in water before step d.

12. The method for preparing the pharmaceutical liquid composition according to claim 11, wherein the amount of viscosity enhancing agent comprising hydroxyethylcellulose added to the glycerol during step b. is selected such that the concentration of the viscosity enhancing agent in the resulting mixture is in the range of 0.01 g/ml to 0.10 g/ml.

13. The pharmaceutical liquid formulation according to claim 1, wherein the pharmaceutical liquid composition is adapted for administration by a nasogastric and/or gastronomy tube.

14. A method for administering the pharmaceutical liquid composition of claim 1 to a patient in need thereof, the method comprising:

a. adding an amount of the pharmaceutical liquid composition to water to form a mixture, wherein the volume ratio between the pharmaceutical liquid composition and water is in the range of 1:20 to 1:1; and b. orally administering said mixture to the patient.

15. The method according to claim 14, wherein the pharmaceutical liquid composition is administered daily to the patient.

16. The method according to claim 15, wherein the amount of the pharmaceutical liquid composition added in step a. to water is in the range 0.5 ml to 20.0 ml.

17. The method according to claim 14, wherein the pharmaceutical liquid composition is part of a kit of parts comprising:

the pharmaceutical liquid composition; and at least one flavouring liquid concentrate, the flavouring concentrate comprising at least one flavouring agent.

18. The method according to claim 17, wherein the kit of parts comprises at least two flavouring liquid concentrates.

19. The pharmaceutical liquid composition of claim 1, wherein the physiologically acceptable salt of 4-phenylbutyric acid is a sodium salt.

20. The pharmaceutical liquid composition of claim 1, wherein the volume concentration of glycerol is in a range of 5.0 ml/l to 20.0 ml/l relative to the total volume of the aqueous medium.

21. The kit of claim 7, wherein the kit comprises a first flavouring agent and a second flavouring agent.

22. The method of claim 17, wherein the kit comprises a first flavouring agent and a second flavouring agent.

23. The method according to claim 17, further comprising adding an amount of at least one flavouring liquid concentrate to the mixture of step a. or to the water used in step a. to form the mixture, before b. orally administering said mixture to the patient.

* * * * *